US009232887B2

(12) United States Patent
Goto et al.

(10) Patent No.: US 9,232,887 B2
(45) Date of Patent: Jan. 12, 2016

(54) OPHTHALMIC APPARATUS AND OPHTHALMIC METHOD

(71) Applicant: CANON KABUSHIKI KAISHA, Tokyo (JP)

(72) Inventors: Atsushi Goto, Miura-gun (JP); Makoto Sato, Tokyo (JP); Hiroyuki Shinbata, Tama (JP)

(73) Assignee: Canon Kabushiki Kaisha, Tokyo (JP)

( * ) Notice: Subject to any disclaimer, the term of this patent is extended or adjusted under 35 U.S.C. 154(b) by 25 days.

(21) Appl. No.: 14/155,222

(22) Filed: Jan. 14, 2014

(65) Prior Publication Data

US 2014/0198300 A1 Jul. 17, 2014

(30) Foreign Application Priority Data

Jan. 16, 2013 (JP) ................................ 2013-005393
Jan. 8, 2014 (JP) ................................ 2014-001524

(51) Int. Cl.

| | |
|---|---|
| ***A61B 3/14*** | (2006.01) |
| ***A61B 3/00*** | (2006.01) |
| ***A61B 3/10*** | (2006.01) |
| ***A61B 3/12*** | (2006.01) |
| ***A61B 5/00*** | (2006.01) |
| ***G01B 9/02*** | (2006.01) |

(52) U.S. Cl.

CPC ............ *A61B 3/0025* (2013.01); *A61B 3/0058* (2013.01); *A61B 3/102* (2013.01); *A61B 3/1225* (2013.01); *A61B 5/0066* (2013.01); *G01B 9/0203* (2013.01); *G01B 9/02027* (2013.01); *G01B 9/02044* (2013.01); *G01B 9/02076* (2013.01); *G01B 9/02091* (2013.01); *G01B 2290/45* (2013.01); *G01B 2290/70* (2013.01)

(58) Field of Classification Search

USPC .................................................. 351/200–246

See application file for complete search history.

(56) References Cited

U.S. PATENT DOCUMENTS

| | | | |
|---|---|---|---|
| 2007/0252951 | A1 | 11/2007 | Hammer |
| 2011/0134436 | A1 | 6/2011 | Podoleanu |
| 2011/0267340 | A1 | 11/2011 | Kraus |

(Continued)

FOREIGN PATENT DOCUMENTS

| | | | |
|---|---|---|---|
| EP | 2392915 | A1 | 12/2011 |
| JP | 2012-161382 | A | 8/2012 |
| WO | 2010/122118 | A1 | 10/2010 |

OTHER PUBLICATIONS

Erich Götzinger, Michael Pircher, Christoph K. Hitzenberger, High Speed Spectral Domain Polarization Sensitive Optical Coherence Tomography of the Human Retina, Dec. 12, 2005, Optics Express, 13(25):10217-10229, Optical Society of America, Washington, D.C., 2005.

*Primary Examiner* — Mohammed Hasan

(74) *Attorney, Agent, or Firm* — Canon USA, Inc. I.P. Division

(57) ABSTRACT

An ophthalmic apparatus includes a fundus image acquisition unit which acquires a plurality of fundus images acquired by imaging fundus of a subject's eye at different times and at least one fundus image that is fewer than the plurality of fundus images and acquired by imaging fundus of the subject's eye at a different time from those for the plurality of fundus images, a unit which generates a new fundus image by averaging the plurality of fundus images, an extraction unit which extracts a feature region from the generated new fundus image, and a unit which tracks the fundus such that positions of a first polarization tomographic image of the fundus corresponding to the new fundus image and a second polarization tomographic image of the fundus corresponding to the at least one fundus image may be corrected based on the extracted feature region and the at least one fundus image.

15 Claims, 11 Drawing Sheets

(56) References Cited

U.S. PATENT DOCUMENTS

2011/0267581 A1* 11/2011 Nakajima et al. ............. 351/206
2012/0113389 A1 5/2012 Mukai
2012/0140179 A1* 6/2012 Miyasa et al. ................ 351/206
2012/0327423 A1 12/2012 Hanebuchi

* cited by examiner

OPHTHALMIC APPARATUS AND OPHTHALMIC METHOD

BACKGROUND OF THE INVENTION

1. Field of the Invention

The present invention relates to an ophthalmic apparatus and an ophthalmic method.

2. Description of the Related Art

An optical coherence tomography (OCT) using a multiple-wavelength light wave interference can acquire a high resolution tomographic image of a sample (fundus in particular).

In recent years, an ophthalmologic OCT apparatus can acquire not only a normal OCT image in which the shape of a fundus tissue is captured but also a polarization OCT image captured using a polarization parameter (retardation and orientation), which is one of optical characteristics of the fundus tissue.

The polarization OCT can configure the polarization OCT image using the polarization parameter, and can perform distinction and segmentation of the fundus tissue. The polarization OCT uses light modulated into circularly polarized light as measuring beam for observing the sample to detect interfering light split as two orthogonal linear polarizations and generate the polarization OCT image (refer to International Patent Application WO2010/122118A1). However, International Patent Application WO2010/122118A1 discloses no method for improving the quality of a polarization OCT image.

SUMMARY OF THE INVENTION

According to an aspect of the present invention, there is provided an ophthalmic apparatus including a fundus image acquisition unit configured to acquire a plurality of fundus images acquired by imaging fundus of a subject's eye at different times and at least one fundus image that is fewer than the plurality of fundus images and acquired by imaging fundus of the subject's eye at a different time from those for the plurality of fundus images, a unit configured to generate a new fundus image by averaging the plurality of fundus images, an extraction unit configured to extract a feature region from the generated new fundus image, and a unit configured to track the fundus such that positions of a first polarization tomographic image of the fundus corresponding to the new fundus image and a second polarization tomographic image of the fundus corresponding to the at least one fundus image may be corrected on basis of the extracted feature region and the at least one fundus image.

The present invention may improve the quality of a polarization OCT image.

Further features of the present invention will become apparent from the following description of exemplary embodiments with reference to the attached drawings.

DESCRIPTION OF THE EMBODIMENTS

An imaging apparatus according to the present invention is applicable to subjects such as a subject's eye, a skin, and internal organs. The imaging apparatus according to the present invention is an ophthalmologic apparatus and an endoscope, for example. The following describes in detail an ophthalmologic apparatus according to the present exemplary embodiment as an example of the present invention with reference to the attached drawings.

[Overall Configuration of the Apparatus]

Figure 1:
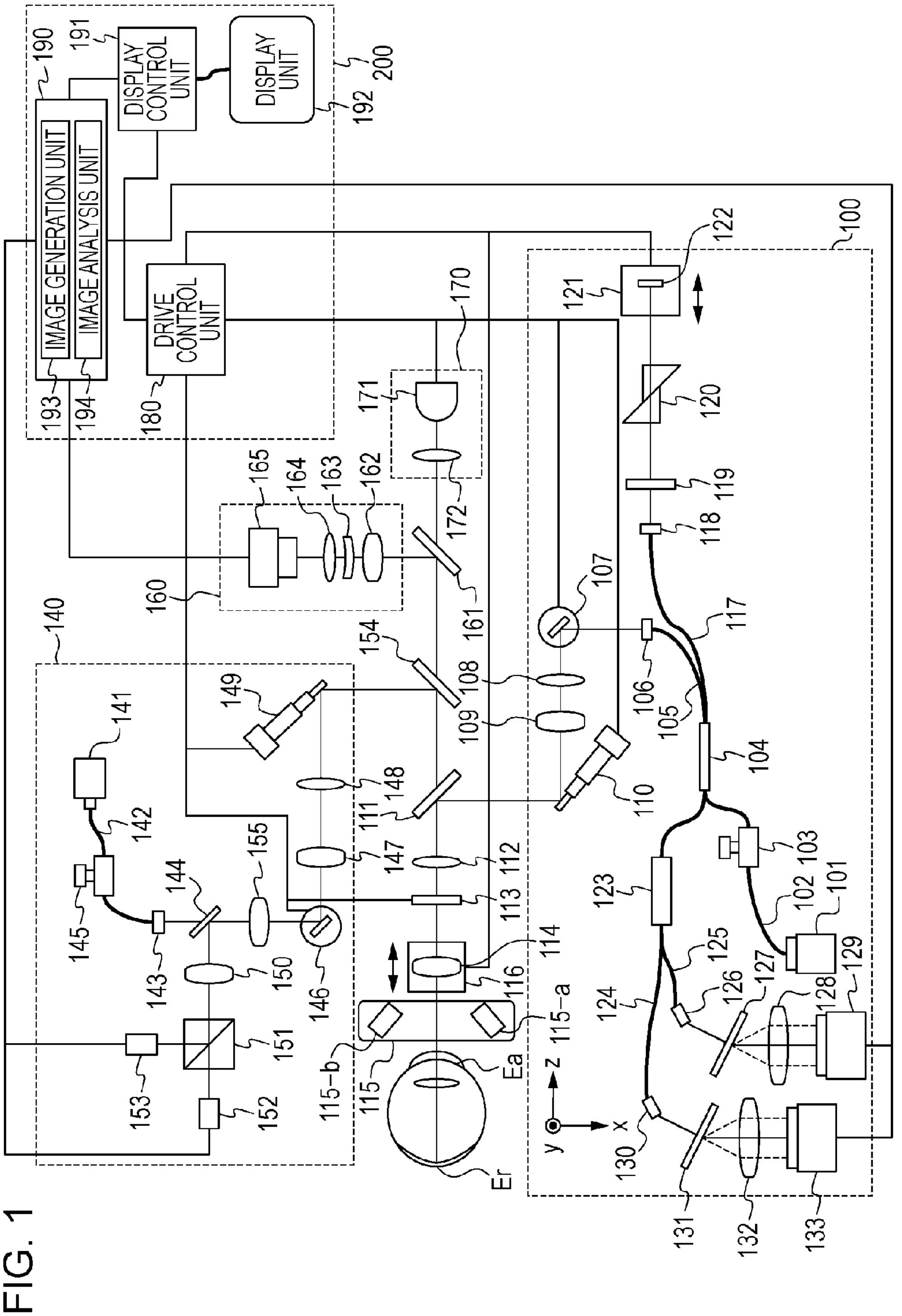
FIG. 1 is a schematic diagram illustrating an overall configuration of an image processing apparatus according to an exemplary embodiment.

FIG. 1 is a schematic diagram illustrating an overall configuration of an "ophthalmologic apparatus" which is an example of an imaging apparatus in the present exemplary embodiment. At least a part of a signal processing unit 190 described below can be regarded as an "image processing apparatus." In this case, the entire "ophthalmologic apparatus" can be regarded as an "ophthalmologic system", or the entire "imaging apparatus" can be regarded as an "imaging system".

The ophthalmologic apparatus includes a polarization sensitive OCT 100 (hereinafter referred to as PS-OCT), a polarization sensitive scanning laser ophthalmoscope 140 (hereinafter referred to as PS-SLO), an anterior eye imaging unit 160, an internal fixation lamp 170, and a control unit 200.

Alignment of the ophthalmologic apparatus is performed using an image at an anterior eye portion of the subject observed by the anterior eye imaging unit 160 with the internal fixation lamp 170 turned on and the subject's eye caused to gaze thereat. After the alignment is completed, the PS-OCT 100 and the PS-SLO 140 perform imaging of the fundus.

<Configuration of OCT 100>

The configuration of the OCT 100 is described.

A light source 101 is a super luminescent diode (SLD) light source low in coherence and emits light with a center wavelength of 850 nm and a band width of 50 nm, for example. Although the SLD is used as the light source 101, any light source which can emit low-coherent light such as an amplified spontaneous emission (ASE) light source, for example, may be used.

The light emitted from the light source 101 is guided to a fiber coupler 104 with a polarization holding function via a polarization maintaining (PM) fiber 102 and a polarization controller 103, and split into a measuring beam (hereinafter referred to as "measuring beam for a tomographic image" or "OCT measuring beam") and a reference beam corresponding to the measuring beam.

The polarization controller 103 is for adjusting the state of light emitted from the light source 101 to linear polarization. The branching ratio of the fiber coupler 104 is 90 (the reference beam) to 10 (the measuring beam).

The measuring beam is emitted as parallel light from a collimator 106 via a PM fiber 105. The emitted measuring beam reaches a dichroic mirror 111 via an X scanner 107 including a galvanometer mirror which scans the measuring beam in the horizontal direction at the fundus Er and a Y scanner 110 including a galvanometer mirror which scans the measuring beam in the vertical direction at lenses 108 and 109 and the fundus Er. The X and Y scanners 107 and 110 are controlled by a drive control unit 180 and can scan the measuring beam in a desired range of the fundus Er. The range in which the measuring beam is scanned on the fundus can be regarded as the acquisition range of the tomographic image, the acquisition position of the tomographic image, and the irradiation position of the measuring beam. The X and Y scanners 107 and 110 are examples of scanning unit for the PS-OCT and may be configured as a common XY scanner. The dichroic mirror 111 has a characteristic that reflects light with a wavelength of 800 nm to 900 nm and transmits the rest.

The measuring beam reflected by the dichroic mirror 111 passes through a λ/4 polarizing plate which is arranged with an angle of 45° tiled from P polarization to S polarization with an optical axis as a rotation axis via a lens 112 to shift the phase of the measuring beam by 90°, and is polarization controlled to a circularly polarized light. The λ/4 polarizing plate is an example of a polarization adjustment member for the measuring beam for adjusting the polarization state of the measuring beam. If the PS-SLO optical system described below is applied, the λ/4 polarizing plate 113 can be provided in a common optical path of a part of the PS-OCT optical system and a part of the PS-SLO optical system. This allows comparatively suppressing the dispersion of polarization state occurring on the image acquired by the PS-SLO optical system and the image acquired by the PS-OCT optical system. At this point, the scanning units for the PS-SLO and the PS-OCT are provided in positions conjugate to each other and can be provided in positions conjugate to the pupil of the subject's eye. The tilt of the λ/4 polarizing plate 113 is an example of state of the λ/4 polarizing plate 113 and an angle from a predetermined position with the optical axis of a polarization split face of a fiber coupler 123 incorporating a polarization beam splitter as a rotation axis, for example.

The measuring beam reflected by the dichroic mirror 111 passes through a λ/4 polarizing plate which is arranged with an angle of 45° tiled from P polarization to S polarization with an optical axis as a rotation axis via a lens 112 to shift the phase of the measuring beam by 90°, and is polarization controlled to a circularly polarized light. The λ/4 polarizing plate is an example of a polarization adjustment member for the measuring beam for adjusting the polarization state of the measuring beam. If the PS-SLO optical system described below is applied, the λ/4 polarizing plate 113 can be provided in a common optical path of a part of the PS-OCT optical system and a part of the PS-SLO optical system. This allows comparatively suppressing the dispersion of polarization state occurring on the image acquired by the PS-SLO optical system and the image acquired by the PS-OCT optical system. At this point, the scanning units for the PS-SLO and the PS-OCT are provided in positions conjugate to each other and can be provided in positions conjugate to the pupil of the subject's eye. The tilt of the λ/4 polarizing plate 113 is an example of state of the λ/4 polarizing plate 113 and an angle from a predetermined position with the optical axis of a polarization split face of a fiber coupler 123 incorporating a polarization beam splitter as a rotation axis, for example.

The light incident on the subject's eye is polarization-controlled to a circularly polarized light by arranging the λ/4 polarizing plate tilted by 45°, however, the light may not be controlled to the circularly polarized light at the fundus Er depending on the characteristics of the subject's eye. For that reason, the tilt of the λ/4 polarizing plate can be fine-adjusted by controlling the drive control unit 180.

The measuring beam which is polarization-controlled to a circularly polarized light is focused on the retinal layer of the fundus Er via the anterior eye portion Ea of eye, which is the subject, by a focus lens 114 mounted on a stage 116. The measuring beam with which the fundus Er is irradiated is reflected and scattered by each retinal layer and returns to the fiber coupler 104 via the above optical path.

The reference beam branched by the fiber coupler 104 is emitted as a parallel light from a collimator 118 via a PM fiber 117. As is the case with the measuring beam, the emitted reference beam is polarization-controlled by a λ/4 polarizing plate 119 which is arranged at an angle of 22.5° tiled from P polarization to S polarization with an optical axis as a rotation axis. The λ/4 polarizing plate 119 is an example of a polarization adjustment member for the reference beam for adjusting the polarization state of the reference beam. The reference beam passes through a dispersion compensation glass 120, is reflected by a mirror 122 on a coherence gate stage 121, and returns to the fiber coupler 104. This means that the reference beam passes through the λ/4 polarizing plate 119 twice to cause linear polarization light to return to the fiber coupler 104.

The coherence gate stage 121 is controlled by a drive control unit 180 to cope with difference in eye's axial length. A coherence gate refers to a position corresponding to an optical path length of the reference beam in the optical path of the measuring beam. In the present exemplary embodiment, the optical path length of the reference beam is changed, however, a difference in an optical path length between the optical paths of the measurement and the reference beam has only to be changed.

The light returning to the fiber coupler 104 is combined with the reference beam to be interfering light (hereinafter referred also to as "combined light"). The interfering light is incident on the fiber coupler 123 incorporating the polarization beam splitter. The polarization beam splitter splits the interfering light into P and S polarized light which are different in a polarization direction with a split ratio of 50:50.

The P polarized light passes through a PM fiber 124 and a collimator 130, is separated by a grating 131, and received by a lens 132 and a line camera 133. Similarly, the S polarized light passes through a PM fiber 125 and a collimator 126, is separated by a grating 127, and received by a lens 128 and a line camera 129. The gratings 127 and 131 and the line cameras 129 and 133 are arranged in the direction according to each polarized light.

The light received by each of the line cameras 129 and 133 is output as an electric signal according to the strength of the light and received by a signal processing unit 190 being an example of a tomographic image generation unit.

The tilts of the λ/4 polarizing plates 113 and 119 can be automatically adjusted based on the tilt of polarization split face of the polarization beam splitter, but may be automatically adjusted with reference to a straight line connecting the center of optic disk of the fundus with the center of macula lutea of the fundus. It is desirable to have a tilt detection unit (not illustrated) for detecting the tilts of the λ/4 polarizing plates 113 and 119. The tilt detection unit can detect a present tilt and a predetermined tilt. Needless to say, the tilts of the λ/4 polarizing plates 113 and 119 may be detected based on the strength of the received light to adjust the tilts thereof so that a predetermined strength of light can be acquired. As described below, an object indicating the tilt is displayed on a graphic user interface (GUI) and a user may adjust the tilt using a mouse. The polarization beam splitter and the λ/4 polarizing plates 113 and 119 are adjusted with reference to the perpendicular direction as a polarization reference to acquire the similar effect.

<Configuration of PS-SLO 140>

The configuration of the PS-SLO 140 is described below.

A light source 141 is a semiconductor laser and emits light whose center wavelength is 780 nm, for example, in the present exemplary embodiment. The measuring beam emitted from the light source 141 (hereinafter referred to as "measuring beam for fundus image" or "SLO measuring beam") passes through a PM fiber 142, is polarization controlled to a linearly polarized light by a polarization controller 145, and emitted as parallel light from a collimator 143. The emitted light passes through a hole portion of a perforated mirror 144 and reaches a dichroic mirror 154 via a lens 155, an X scanner 146 including a galvanometer mirror which scans the measuring beam into the horizontal direction at the fundus Er, lenses 147 and 148, and a Y scanner 149 including a galvanometer mirror which scans the measuring beam into the vertical direction at the fundus Er. The X and Y scanners 146 and 149 are controlled by the drive control unit 180 and can scan a desired range on the fundus using the measuring beam. The X and Y scanners 146 and 149 are examples of the scanning unit for the PS-SLO and may be configured as a common XY scanner. The dichroic mirror 154 has a characteristic that reflects light with a wavelength of 760 nm to 800 nm and transmits the rest.

The measuring beam of liner polarization reflected by the dichroic mirror 154 passes through the same optical path as the measuring beam of the PS-OCT 100 and reaches the fundus Er.

The measuring beam with which the fundus Er is irradiated is reflected and scattered at the fundus Er, and reaches the perforated mirror 144 via the above-described optical path. The light reflected by the perforated mirror 144 passes through a lens 150, is split by a polarization beam splitter 151 into light different in polarization direction (P polarized light and S polarized light in the present exemplary embodiment), received by avalanche photo diodes (APD) 152 and 153, converted into a electric signal, and received by the signal processing unit 190, which an example of a fundus image generation unit.

The position of the perforated mirror 144 is conjugate to the position of a pupil of the subject's eye. The light passing through the periphery of the pupil among light in which the measuring beam with which the fundus Er is irradiated is reflected and scattered is reflected by the perforated mirror 144.

In the present exemplary embodiment, both of the PS-OCT and the PS-SLO use the PM fiber, however, the use of a single mode fiber (SMF) allows acquiring similar configuration and effect by controlling polarization using the polarization controller.

<Anterior Eye Imaging Unit 160>

The anterior eye imaging unit 160 is described.

In the anterior eye imaging unit 160, the anterior eye portion Ea is irradiated by an illumination light source 115 composed of light emitting diodes (LED) 115-*a* and 115-*b* emitting illumination light with a wavelength of 1000 nm. The light reflected by the anterior eye portion Ea reaches a dichroic mirror 161 via the lens 114, the polarizing plate 113, the lens 112, and the dichroic mirrors 111 and 154. The dichroic mirror 161 has a characteristic that reflects light with a wavelength of 980 nm to 1100 nm and transmits the rest. The light reflected by the dichroic mirror 161 is received by an anterior eye camera 165 via lenses 162, 163, and 164. The light received by the anterior eye camera 165 is converted into an electric signal and received by the signal processing unit 190.

<Internal Fixation Lamp 170>

The internal fixation lamp 170 is described.

The internal fixation lamp 170 includes an internal fixation-lamp display unit 171 and a lens 172. A plurality of light emitting diodes (LD) arranged in a matrix form is used as the internal fixation-lamp display unit 171. A position where to turn on the light emitting diodes is changed according to a site desired to be imaged by controlling the drive control unit 180. The light emitted from the internal fixation-lamp display unit 171 is guided to the subject's eye via the lens 172. The light emitted from the internal fixation-lamp display unit 171 has a wavelength of 520 nm and a desired pattern is displayed by the drive control unit 180.

<Control Unit 200>

The control unit 200 for controlling the entire apparatus is described below.

The control unit 200 includes the drive control unit 180, the signal processing unit 190, a display control unit 191, and a display unit 192.

The drive control unit 180 controls each unit as described above.

The signal processing unit 190 includes an image generation unit 193 and an image analysis unit 194. The signal processing unit 190 generates an image, analyzes the generated image, and generates visualization information of the analysis result based on the signals output from the line cameras 129 and 133, the APDs 152 and 153, and the anterior eye camera 165. The generation and analysis of an image are described below in detail.

The display control unit 191 displays on display unit 192 the images generated by the tomographic image generation unit and the fundus image generation unit and acquired by a fundus image acquisition unit (not illustrated) and a tomographic image acquisition unit (not illustrated) respectively on a display screen. The display unit 192 is a liquid crystal display, for example. The image data generated by the signal processing unit 190 may be transmitted by wire to the display control unit 191 or by wireless. In this case, the display control unit 191 can be regarded as an image processing apparatus. As an image system, the fundus image acquisition unit may include the SLO optical system, and the tomographic image acquisition unit may include the OCT optical system. In this specification, for the case of a subject except the subject's eye, a "fundus image (fundus luminance image)" may be paraphrased in a "planar image (planar luminance image)" and the "fundus image acquisition unit" may be paraphrased in a "planar image acquisition unit".

The display unit 192 displays display forms indicating various pieces of information described below under the control of the display control unit 191. The image data from the display control unit 191 may be transmitted by wire to the display unit 192 or by wireless. The display unit 192 is included in the control unit 200, however, the present invention is not limited thereto, and the display unit 192 may be provided separately from the control unit 200. Alternatively, a tablet may be provided, which is an example of a user portable apparatus into which the display control unit 191 and the display unit 192 are integrated. In this case, it is desirable to mount a touch panel function on the display unit to allow moving the display position of an image, expanding and reducing the image and changing the displayed image on the touch panel.

[Image Processing]

The image generation by the image generation unit 193 included in the signal processing unit 190 is described below.

The image generation unit 193 subjects the interference signals output from the line cameras 129 and 133 to a reconfiguration processing used in a general spectral domain OCT (SD-OCT) to generate tomographic images corresponding to a first and a second polarized light which are two tomographic images based on each polarization component.

The image generation unit 193 reduces a fixed pattern noise from the interference signal. The fixed pattern noise is reduced in such a manner that a plurality of the detected A scan signals is averaged to extract the fixed pattern noise, and the extracted fixed pattern noise is subtracted from the input interference signal.

The image generation unit 193 converts the interference signal from wavelength to the number of waves and performs Fourier-transform thereof to generate a tomographic signal indicating a polarization state.

The interference signal of two polarization components is subjected to the above processing to generate two tomographic images.

The image generation unit 193 aligns the signals output from the APDs 152 and 153 in synchronization with the drive of the X and Y scanners 146 and 149 to generate fundus images corresponding to the first and the second polarized light which are two fundus images based on each polarization component.

<Generation Of Tomographic Luminance Image Or Fundus Luminance Image>

The image generation unit 193 generates the tomographic luminance image from the two tomographic signals.

The tomographic luminance image is basically the same as the tomographic image in the conventional OCT. The pixel value r is calculated from the tomographic signals $A_H$ and $A_V$ acquired from the line sensors 129 and 133 by an equation 1:

$$r = \sqrt{A_H^2 + A_V^2} \quad (1)$$

Similarly, the image generation unit 193 generates the fundus luminance image from the two fundus luminance images.

Figure 2A:
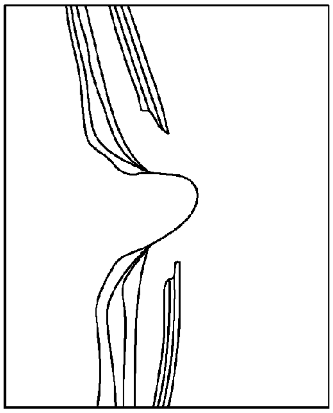
FIGS. 2A to 2E illustrate examples of images generated by a signal processing unit 190.

FIG. 2A illustrates an example of a luminance image of an optic disk portion.

The display control unit 191 may cause the display unit 192 to display the tomographic luminance image acquired by a conventional OCT method on the display unit 192 if the λ/4 polarizing plate 113 is removed from the optical path or the fundus luminance image acquired by a conventional SLO method on the display unit 192.

<Generation of Retardation Image>

The image generation unit 193 generates a retardation image from a tomographic image of polarization components orthogonal to each other.

A value δ of each pixel of the retardation image is a value indicating a ratio of influence of vertical and horizontal polarization components on the subject's eye in a position of each pixel forming the tomographic image. The value δ is calculated from the tomographic signals $A_H$ and $A_V$ by an equation 2:

$$\delta = \arctan\left[\frac{A_V}{A_H}\right] \quad (2)$$

Figure 2B:
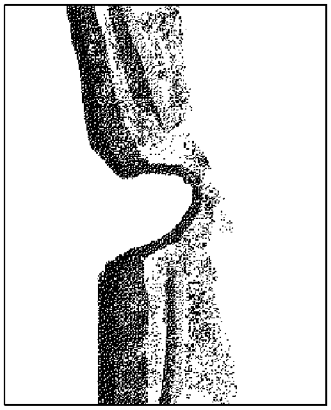

FIG. 2B illustrates an example of a retardation image of thus generated optic disk portion, and the retardation image can be obtained by the equation 2 for each B scan image. As described above, the retardation image refers to the tomographic image indicating a difference in influence of two polarizations on the subject's eye. In FIG. 2B, the value indicating the ratio is displayed in color as the tomographic image. Places where shading is thick are small in value indicating the ratio. Places where shading is thin are large in value indicating the ratio. For this reason, the generation of the retardation image allows a birefringent layer to be recognized. The details are as discussed in "E. Gotzinger et al., Opt. Express 13, 10217, 2005".

Similarly, the signal processing unit 190 can also generate the retardation image in the planar direction of the fundus based on the output from the APDs 152 and 153.

<Generation Of Retardation Map>

The image generation unit 193 generates a retardation map from the retardation image acquired from a plurality of B scan images.

The image generation unit 193 detects a retinal pigment epithelium (hereinafter referred to as "RPE") in each B scan image. The RPE has the property of dissolving polarization, so that the distribution of retardation is examined along a depth direction without the range from an internal limiting membrane (hereinafter referred to as "ILM") to the RPE by each A scan and the maximum value of the retardation is taken as the representative value of the retardation in the A scan.

The image generation unit 193 performs above processing on all retardation images to generate a retardation map.

Figure 2C:
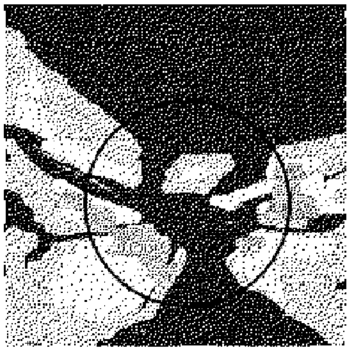

FIG. 2C illustrates an example of the retardation map of the optic disk portion. Places where shading is thick are small in value indicating the ratio. Places where shading is thin are large in value indicating the ratio. In the optic disk portion, a layer with birefringence is a retinal nerve fiber layer (hereinafter, referred also to as "RNFL"). The retardation map is an image indicating a difference in influence which two polarizations receive according to the birefringence of the RNFL and the thickness of the RNFL. For this reason, the value indicating the ratio is increased at a place where the RNFL is thick and decreased at a place where the RNFL is thin. Therefore, with the retardation map, the thickness of the RNFL all over the fundus can be recognized, and the retardation map can be used for the diagnosis of glaucoma.

<Generation of Birefringence Map>

The image generation unit 193 linearly approximates the value of the retardation δ in the range from the ILM to the RNFL in each A scan image of the previously generated retardation image and determines the tilt of the retardation δ as birefringence in a position on the retina of the A scan image. In other words, the retardation is the product of distance and birefringence in the RNFL, so that the values of depth and retardation in each A scan image are plotted to acquire a linear relationship. Therefore, if the tilt is acquired by linearly approximating the plot using the least squares method, the tilt is a value of the birefringence of the RNFL in the A scan image. All the retardation images are subjected to the processing to generate the map indicating birefringence.

Figure 2D:

FIG. 2D illustrates an example of the birefringence map of the optic disk portion. Because birefringence values are directly mapped, the birefringence map can describe a fiber structure as a change in birefringence if the fiber structure is changed even if the thickness of the RNFL is not changed.

<Generation of DOPU Image>

The image generation unit 193 calculates a Stokes vector S for each pixel from the acquired tomographic signals $A_H$ and $A_V$ and a phase difference $\Delta\phi$ between the tomographic signals using an equation 3.

$$s = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\phi \\ 2A_H A_V \sin\Delta\phi \end{pmatrix} \quad (3)$$

where, the phase difference $\Delta\phi$ is calculated from phases $\phi_H$ and $\phi_V$ of each signal acquired when two tomographic signals are calculated as $\Delta\phi=\phi_V-\phi_H$.

Figure 2E:
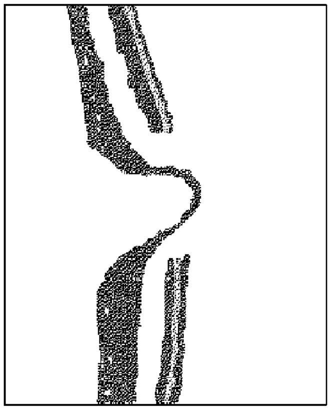

The image generation unit 193 sets a window with a size of about 70 μm in the main scanning direction of the measuring beam and about 18 μm in the depth direction thereof in each B scan image, averages each element of a stroke vector calculated for each pixel by a number C in each window and calculates the degree of polarization uniformity (DOPU) of polarization in the window using an equation 4.

$$DOPU=\sqrt{Q_m^2+U_m^2+V_m^2} \quad (4)$$

where, $Q_m$, $U_m$, and $V_m$ are values in which the elements Q, U, and V of the stroke vector in each window are averaged. All the windows in the B scan image are subjected to the processing to generate the DOPU image of the optic disk portion illustrated in FIG. 2E. As described above, the DOPU image is the tomographic image indicating the degree of uniformity of two polarizations.

The DOPU is a value indicating the degree of uniformity of polarization and is the value near to 1 in a place where polarization is maintained, but is the value smaller than 1 in a place where polarization is dissolved and not maintained. In a structure of a retina, the RPE has the property of dissolving polarization, so that the value is smaller than that in other areas in a portion corresponding to the RPE in the DOPU image. In FIGS. 2A to 2E, a place where shading is thin represents the RPE and a place where shading is thick represents the area of the retinal layer where change is maintained. The DOPU image images a layer canceling polarization such as the RPE, so that the DOPU image can more surely image the RPE than change in luminance even if the RPE is deformed due to disease.

Similarly, the signal processing unit 190 can also generate the DOPU image in the planar direction of the fundus based on the output from the APDs 152 and 153.

In the present specification, the tomographic image, the retardation image, and the DOPU image corresponding to the first and the second polarization described above are also referred to as a tomographic image representing the polarization state. Also in the present specification, the retardation map and the birefringence map described above are also referred to as a fundus image representing the polarization state.

[Processing operation]

The processing operation of the image processing apparatus is described below.

Figure 3:
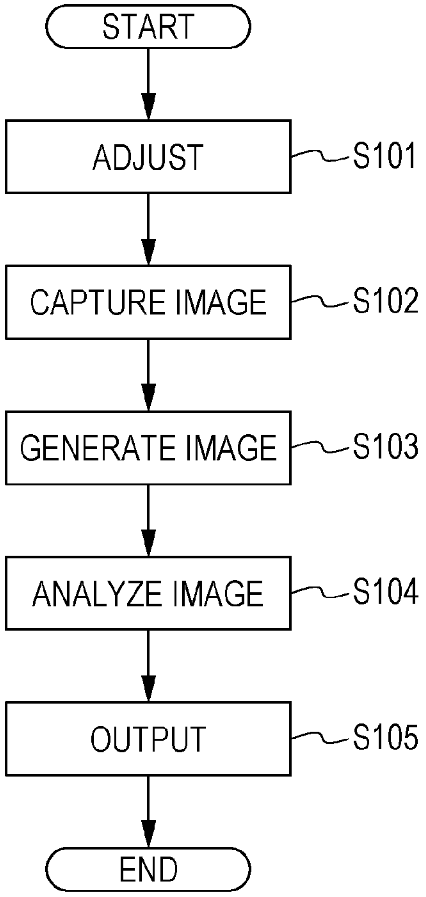
FIG. 3 is a flow chart illustrating a processing flow according to the exemplary embodiment.

FIG. 3 is a flow chart illustrating the processing operation of the image processing apparatus.

[Adjustment]

In step S101, the subject's eye is placed on the apparatus and the apparatus is aligned with the subject's eye. For the description of alignment, only specific processing of the present exemplary embodiment is described. The descriptions of alignment in the XYZ directions such as working distance, and the adjustment of focus and coherence gate are omitted because they are general.

<Capture Image>

A movement of a subject's eye due to an involuntary eye movement or poor fixation during PS-OCT imaging may distort a resulting PS-OCT image. In order to prevent this, a tracking operation which causes the movement of an OCT scanner to follow the movement of the eye is performed during PS-OCT imaging in step S102.

Figure 10:
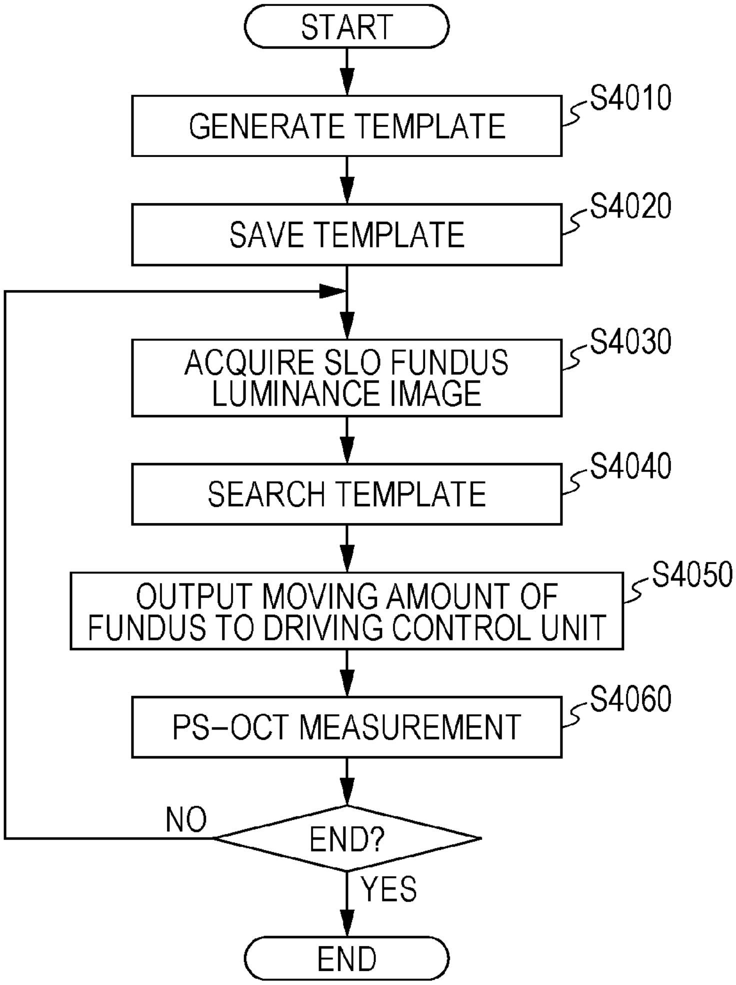
FIG. 10 is a flow chart illustrating a flow of processing according to the exemplary embodiment.

FIG. 10 is a detail flow chart illustrating a flow of step S102 (Capture Image) according to the exemplary embodiment, and the processing in step S102 will be described with reference to the flow chart in FIG. 10. FIG. 10 illustrates steps S4010 to S4050 for implementing a tracking function. A tracking control unit 195 is responsible for the tracking function.

Figure 11:
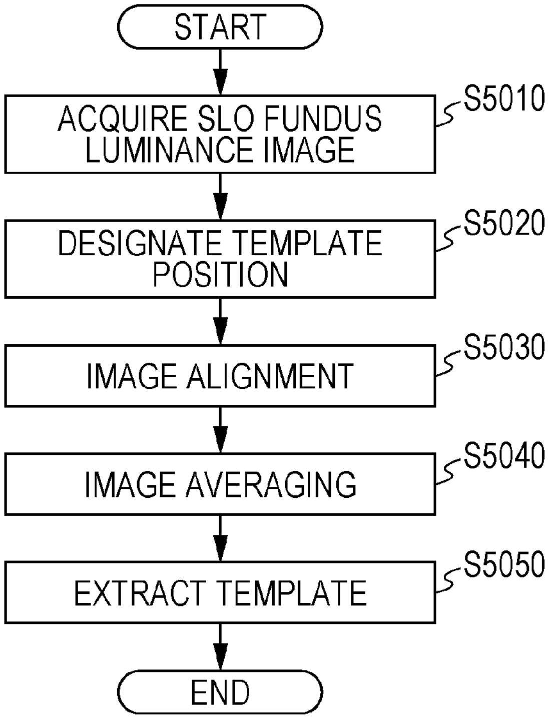
FIG. 11 is a flow chart illustrating a flow of processing according to the exemplary embodiment.

Step S4010 (Generate Template) in FIG. 10 follows the flow of processing illustrated in FIG. 11 in detail. In step S4010, a template image to be used for template matching is generated.

First, in step S5010 (Acquire SLO Fundus Luminance Image), the tracking control unit 195 acquires 20 frames of generated SLO fundus luminance images from the APDs 152 and 153 for template generation.

As the number of frames of SLO fundus luminance images for template generation increases, the image quality of a template image generated through image averaging performed in step S5040 improves, resulting in improved accuracy of template matching. On the other hand, a higher number of SLO fundus luminance images for template generation may increase the processing time for template generation. 20 or more frames may be selected for the accuracy necessary for OCT photographing though the number of frames may be determined in consideration of the necessary accuracy of matching and processing speed.

Figure 12:
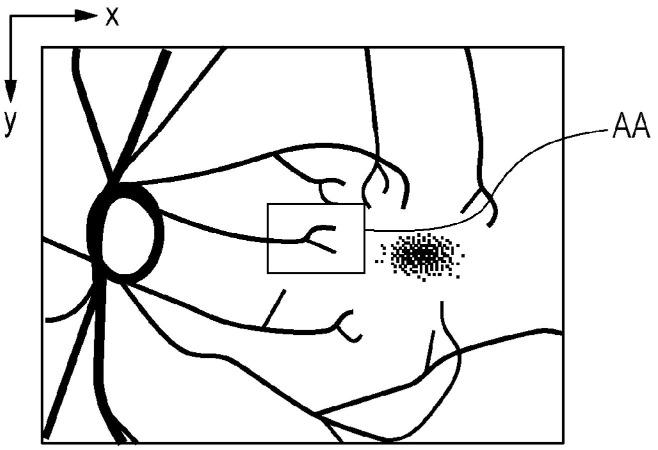
FIG. 12 is a diagram illustrating designation of a template position for tracking according to the exemplary embodiment.

Next, in step S5020 (Designate Template Position), the tracking control unit 195 displays the SLO fundus luminance images acquired in step S4010 on the display unit 192 through the display control unit. An operator may manually designate an image area to be used as a template by using a mouse. FIG. 12 illustrates an example of a designated template position. FIG. 12 illustrates an SLO fundus luminance image in which the area AA corresponds to a template-designated area.

An area having a characteristic pattern such as a position having a diverging blood vessel may be selected as the template-designated area AA because it is used for pattern matching.

A plurality of template areas may be selected. When two or more template areas are selected, a moving amount may be calculated with high accuracy by averaging shift amounts X and Y acquired as a result of template matching.

The template position designation may be performed automatically by the tracking control unit 195. In this case, Harris Corner Detection Algorithm may be used as an algorithm for selecting an area having a characteristic pattern.

Alternatively, Moravec Corner Detection Algorithm or other corner detection algorithms may be used as an algorithm for selecting an area having a characteristic pattern. Automatic selection of a plurality of templates may allow quick selection of a template position having a characteristic pattern.

Next, in step S5030 (Image Alignment), the tracking control unit 195 calculates registration error amounts of the 20 frames for template generation acquired in step S5010 and aligns the image patterns. The tracking control unit 195 determines an image of one of the frames acquired in step S5010 as a template and performs template search through the remaining 19 frames. More specifically, the tracking control unit 195 calculates a Normalized Cross-Correlation (NCC) that is an index representing a similarity at different positions on a template image, acquires a difference between image positions with a maximum index value as a registration error amount, and aligns images of the 20 frames.

The index representing a similarity may be any measure representing a similarity of a characteristic between a template and an image within a frame. For example, Sum of Absolute Difference (SAD), Sum of Squared Difference (SSD), Zero-means Normalized Cross-Correlation (ZNCC) or the like may be used.

Next in step S5040 (Image Averaging), the tracking control unit 195 averages the images aligned by step S5030 for the 20 frames of images acquired for template generation in step S5010.

Next, in step S5050, the tracking control unit 195 extracts an image on basis of information on the template position selected in step S5020 from the aligned and averaged images generated in step S5040. The extracted image is a template image to be used for template matching. The template generation in step S4010 has been described in detail up to this point.

In step S4020 (Save Template) in FIG. 10, the tracking control unit 195 saves the template generated in step S4010 in a storage unit (not illustrated).

Next, in step S4030 (Acquire SLO fundus luminance image), the tracking control unit 195 acquires one frame of an SLO fundus luminance image or a lower number of frames than the number of frames acquired in step S5010 of an SLO fundus luminance image for calculation of a fundus moving amount. A plurality of SLO images for calculating a fundus moving amount may be acquired, be superimposed and be averaged for higher image quality. However, a higher number of SLO images may increase the period of time from a time when an SLO fundus luminance image is first acquired to the time when template matching completes, which may delay the tracking. A higher number of SLO images for calculating a fundus moving amount may reduce the frequency of template matching and may reduce the frequency of OCT position correction (resulting in a lower operating frequency of tracking). From the viewpoint of prevention of tracking delay and prevention of a lower operating frequency, the number of SLO images for calculating a fundus moving amount is desirably lower than the number of frames for template generation acquired in step S5010.

A low-pass filter (LPF) is also applicable to SLO images for calculating a fundus moving amount. A template image resulting from averaging of a plurality of images has a luminance value the fluctuations of which are smoothed. Thus, an LPF may also be applied to SLO images for calculating a fundus moving amount with fluctuations of luminance values smoothed so that the corresponding template image and the SLO images for calculating a fundus moving amount may have a substantially equal spatial frequency for higher accuracy of the template search in S4040. In this case, the factor may be determined in accordance with the number of frames used for generating the template for a substantially equal frequency response of the LPF.

Figure 13:
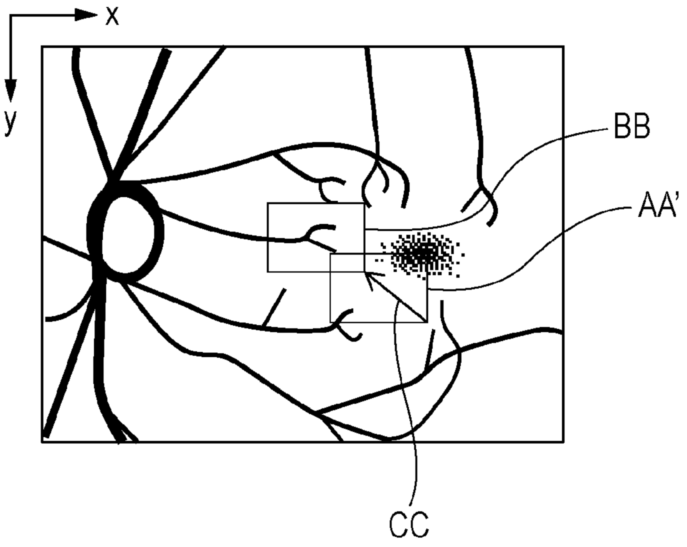
FIG. 13 is a diagram illustrating calculation of a moving amount of fundus according to the exemplary embodiment.

Next, in step S4040 (Search Template), the tracking control unit 195 searches the template image saved in step S4020 from the SLO fundus luminance images for calculating a fundus moving amount acquired in step S4030 on basis of a pattern of a blood vessel, for example, rendered on the image to calculate a fundus moving amount. FIG. 13 illustrates an SLO fundus luminance image for calculating a fundus moving amount. A fundus-moving-amount calculation method will be described with reference to FIG. 13. An area AA' is a template-designated position and corresponds to the position of the area AA in FIG. 12. An area BB is a position resulting from template search. An area CC is a difference between the positions of the areas AA' and BB. The area CC is calculated as a fundus moving amount.

The template search method is the same as the template search method used in step S5030 (Image Alignment).

A similarity index with lower computational complexity may be acquired in consideration of a tracking delay in step S4040.

The amount of rotations θ may be calculated as a fundus moving amount by adding the amounts of shifts X and Y.

Next, in step S4050 (Output Fundus Moving Amount to Driving Control Unit), the tracking control unit 195 outputs the fundus moving amount acquired in step S4040 to the driving control unit 180.

The driving control unit 180 controls the X scanner 107 and Y scanner 110 in accordance with two input X and Y moving amounts such that the OCT photographing position may be constant at all times. Thus, tomographic images resulting from capturing images at a same position may be acquired at all times even when the subject's eye moves due to an involuntary eye movement or poor fixation.

Next, in step S4060 (PS-OCT measurement), the control unit 200 causes the light source 101 to emit measurement light and the line cameras 129 and 133 to receive return light from the retina Er.

An operator may then determine whether to finish or continue the imaging in series. If the PS-OCT imaging is to be continued in series, the tracking control unit 195 returns to step S4030, and steps S4030 to S4060 are repeated.

For tracking of a movement of a subject's eye, the operating rate of the PS-SLO 140 may be faster than the operating rate of the PS-OCT 100. For example, in a case where the B scanning rate of PS-OCT is equal to 15 Hz and if the rate of acquisition and processing of SLO fundus luminance images with a PS-SLO is equal to 60 Hz, position correction may be performed four times during one B scanning operation.

Position correction with a scanner may be performed when an image of a center part of a photographed area is less distorted by a movement of the scanner. The scanning rate or correction timing may be adjusted on basis of the acquisition rates of the PS-OCT and PS-SLO such that the scanner correction may avoid the center of the image.

In order to increase the processing speed, one output from two APDs may only be used instead of SLO fundus luminance images. The PS-SLO may use measurement light having a line shape to scan a fundus, instead of the configuration in FIG. 1. Adopting this configuration may eliminate the necessity for scanning with the X scanner 146, which allows quicker acquisition of SLO fundus luminance images.

According to this embodiment, SLO fundus luminance images are used as an image used for tracking. An SLO luminance image may be acquired with a sum of squares of p-polarized light and s-polarized light, and polarization information on measurement light is not used. Thus, the λ/4 polarizer 113 may be removed from the optical path for acquiring an SLO fundus luminance image for tracking.

According to this embodiment, the PS-SLO 140 includes the X scanner 146 and Y scanner 149 as a galvano scanner to scan a desirable range on a fundus with measurement light and avalanche photodiodes (APD) 152 and 153 as light detecting units for measurement light. However, the Y scanner may only be used as the galvano scanner, and a line sensor may be used as a light detecting unit for measurement light.

<Image Generation>

In step S102 for image capturing, a signal of return light from the retina Er is output to the image generating unit 193, and images are generated in the aforementioned manner.

<Analysis>

The luminance value of the tomographic image of ill eye can be lower than that of the tomographic image of healthy eye due to influence of illness. A retinal layer may be overlooked or erroneously detected due to the influence. For this reason, in step S104, the image analysis unit 194 detects each layer of the retinal layer using information about a place where the polarization state is randomized calculated by the image generation unit 193 in step S103.

Figure 4:
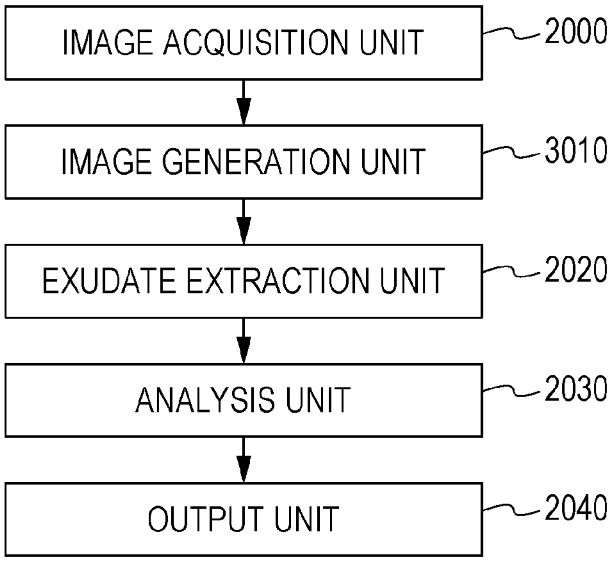
FIG. 4 is a schematic diagram illustrating an example of an image analysis unit.

FIG. 4 illustrates a configuration of the image analysis unit 194. In FIG. 4, an image acquisition unit 2000 is an acquisition unit for acquiring the tomographic image indicating the polarization state generated by the image generation unit 193. The acquisition unit can also be configured to acquire an image from an external server.

A difference image generation unit 3010 and an exudate extraction unit 2020 are extraction units. The difference image generation unit 3010 extracts the RPE as an example of a predetermined layer by analyzing the continuity of a polarization canceling material and subtracts the RPE from the tomographic image indicating the polarization state. The exudate extraction unit 2020 subtracts the predetermined layer from the image and then extracts the exudates.

An analysis unit 2030 acquires information about the position and size of the exudate acquired by the exudate extraction unit 2020. An output unit 2040 outputs processing results to the display control unit 191. The analysis unit 2030 and the output unit 2040 may be included in the display control unit 191.

Figure 5:
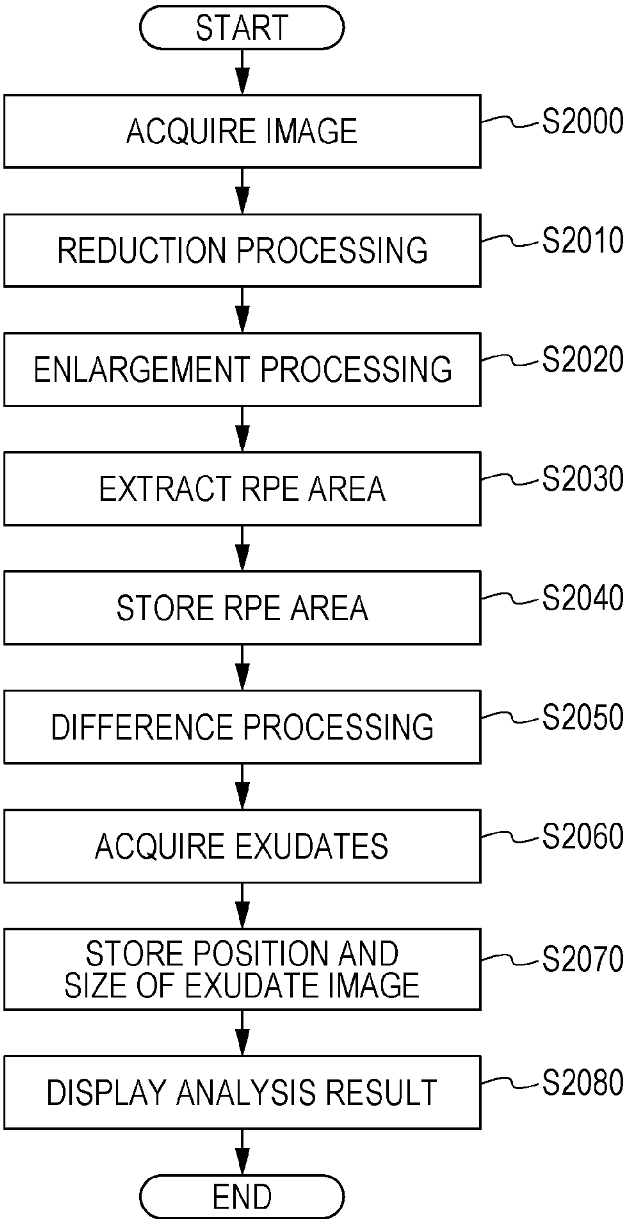
FIG. 5 is a flow chart illustrating a flow of processing according to the exemplary embodiment.

FIG. 5 is a flowchart illustrating a detailed flow of the processing in step S104. The processing in step S104 is described in detail according to the flow of the processing in FIG. 5.

In step S2000, an image acquisition unit 2000 acquires a plurality of three-dimensional tomographic images each indicating a polarization state, which are imaged at different times. A DOPU image acquired by calculating the DOPU using the equation 4 can detect the position of the RPE layer as the predetermined layer because the RPE cancels the polarization state in the retinal layer. The RPE has a layer structure, so that the RPE exists as a mass with a certain capacity or more. On the other hand, exudates often scatter and are smaller than the layer structure such as the RPE.

In step S2010, the difference image generation unit 3010 subjects the area in a pixel value range in a predetermined range to reduction processing by using a filtering processing with a filter such as a morphological filter. For example, a dilation processing is performed. With this processing, exudates disappear. The difference image generation unit 3010 enlarges the reduced image with a reverse processing. For example, an erosion processing is performed. The reverse processing refers to processing to expand an image by the amount equal to the reduction amount. This can provide the layer structure of the RPE. In steps S2030 and S2040, the difference image generation unit 3010 subjects the layer structure of the RPE to binary processing, for example, and stores the area with the predetermined value or more as the area of the RPE layer.

In step S2050, the difference image generation unit 3010 subjects the enlarged image to difference processing with respect to the tomographic image indicating the original polarization state. With this processing, in step S2060, a depolarized area except the RPE layer is acquired (extracted) as exudates. Each image in a depolarized area and information about an area such as the extracted exudates are stored while being associated with the tomographic image indicating the polarization state. Information about imaging time including imaging date and time is also associated with the tomographic image indicating the polarization state. For this reason, each image in the area where the polarization is randomized and information about an area such as the extracted exudates are associated with the imaging time and stored in the storage unit.

The analysis unit 2030 acquires the coordinates of center of gravity in the depolarized area such as exudates acquired from each image. A circumscribed area of the depolarized area such as exudates is acquired and a size of the depolarized area such as exudates is acquired as size. In step S2070, the coordinates of center of gravity in the depolarized area and a size of the depolarized area such as exudates are associated with images such as exudates, and information about the position is associated with the imaging time and stored in the storage unit.

<Output>

Output processing performed in step S105 of the generated images and analysis results is described below. In the output processing according to the present exemplary embodiment, information acquired in step S104 is effectively displayed.

Figure 6:
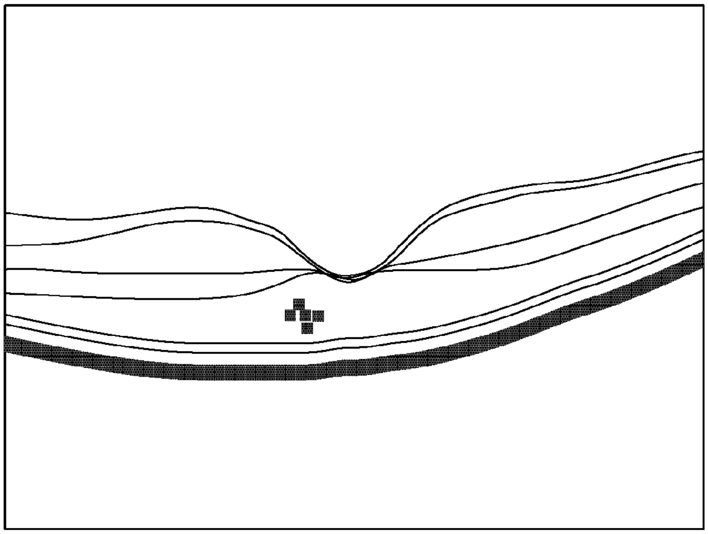
FIG. 6 is an example of display on a display screen of a display unit of the image processing apparatus according to the exemplary embodiment.

When the image generation unit 193 and the image analysis unit 194 in the signal processing unit 190 finish the generation and analysis of each image, the display control unit 191 generates output information based on the results, outputs the output information to the display unit 192 and displays the output information thereon. FIG. 6 is an example in which the display control unit 191 superimposes the image area of the extracted exudates on a two-dimensional tomographic image and displays it on the display unit 192.

Figure 7:
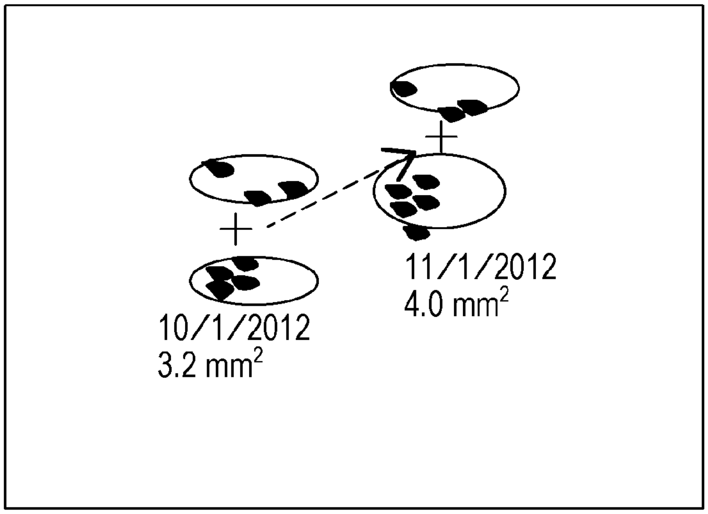
FIG. 7 is an example of display on the display screen of the display unit of the image processing apparatus according to the exemplary embodiment.

The analysis unit 2030 performs accumulation processing on the three-dimensional tomographic image, aligns it with the fundus image, which is a planar image, and associates information about the depolarized area such as the exudates extracted by the extraction unit with the coordinates of the fundus image, and stores the information. The display control unit 191 causes the image in the depolarized area, which is stored in the storage unit and imaged at different times, to correspond to the coordinates of the fundus image, which is a planar image, and displays the image on the display unit 192 as changing image. In this case, a color to be displayed for each corresponding imaging time is changed and displayed on the display unit 192 to make it clear how the depolarized area such as exudates is changed with time. Furthermore, the imaging time corresponding to a changing image is associated therewith and displayed to make it clear how the depolarized area such as exudates is changed with time. Moreover, the position and size of the center of gravity in the depolarized area such as exudates for each imaging time are displayed together to make it understandable how the size and the position are changed with time. FIG. 7 illustrates an example in which an image in an area where the polarization imaged at different imaging times is randomized is displayed correspondingly to the coordinates of the planar image, and the position and size of the center of gravity for each imaging time are displayed together on the display unit. In this case, the image is superimposed onto the fundus image, which is a planar image and displayed make it easy to perform comparison with the fundus image.

Figure 8:
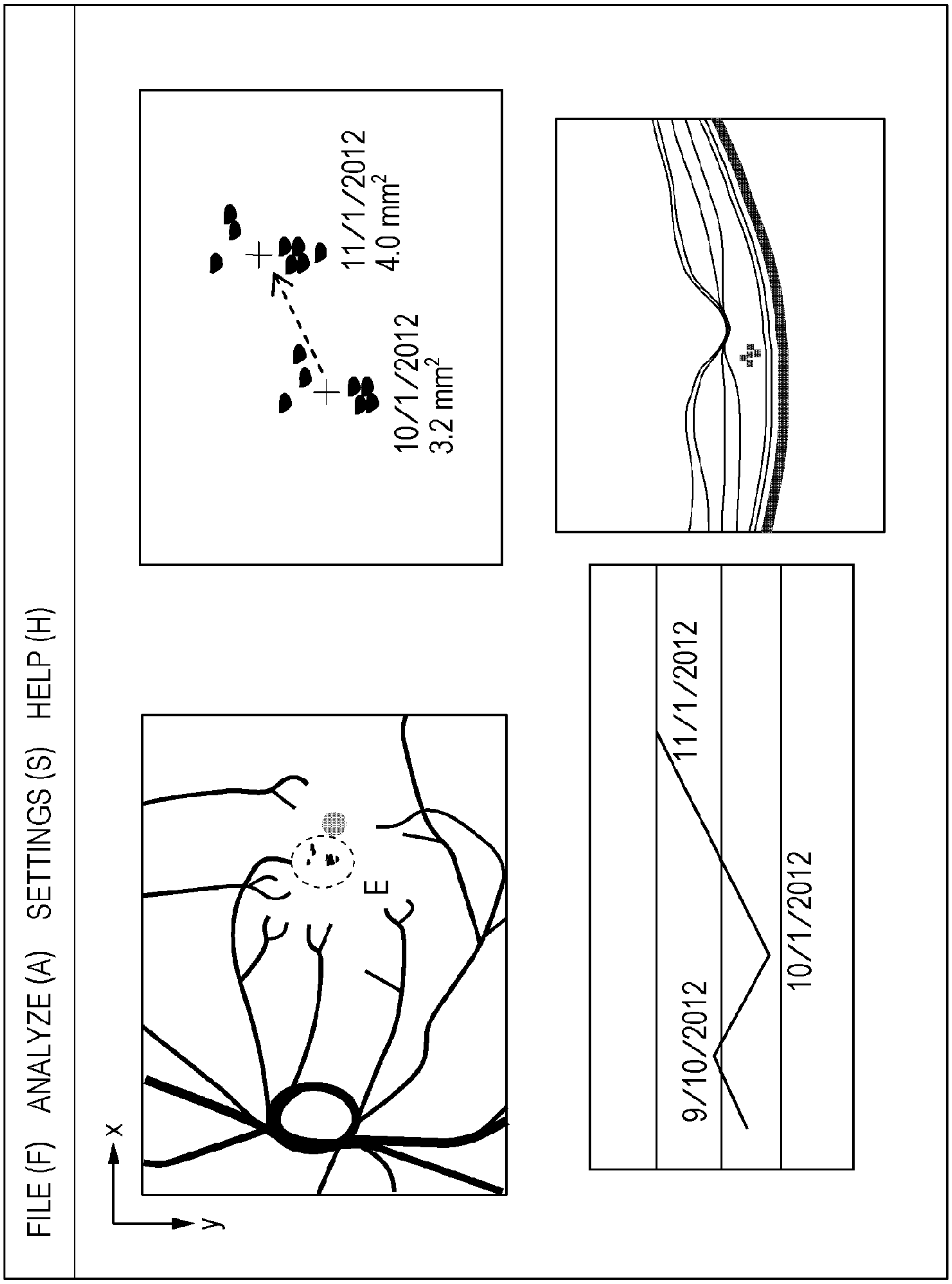
FIG. 8 is an example of display on the display screen of the display unit of the image processing apparatus according to the exemplary embodiment.

The upper left chart in FIG. 8 illustrates the fundus image. The upper right chart therein illustrates an image in a depolarized area is displayed correspondingly to the coordinates of the planar image and a changing image in which the position and size of the center of gravity for each imaging time are displayed together. The lower left chart illustrates a position image displaying the center of gravity as a position of the depolarized area correspondingly to the coordinates of the planar image and imaging time. The lower right chart illustrates the tomographic image crossing the area E where the polarization is randomized such as macula and exudates in the upper left chart. The display control unit 191 displays the images having thus different pieces of information alongside of each other on the display unit 192 to allow observing easily how the depolarized area such as exudates is changed with time.

[Modification Example 1]

Figure 9:
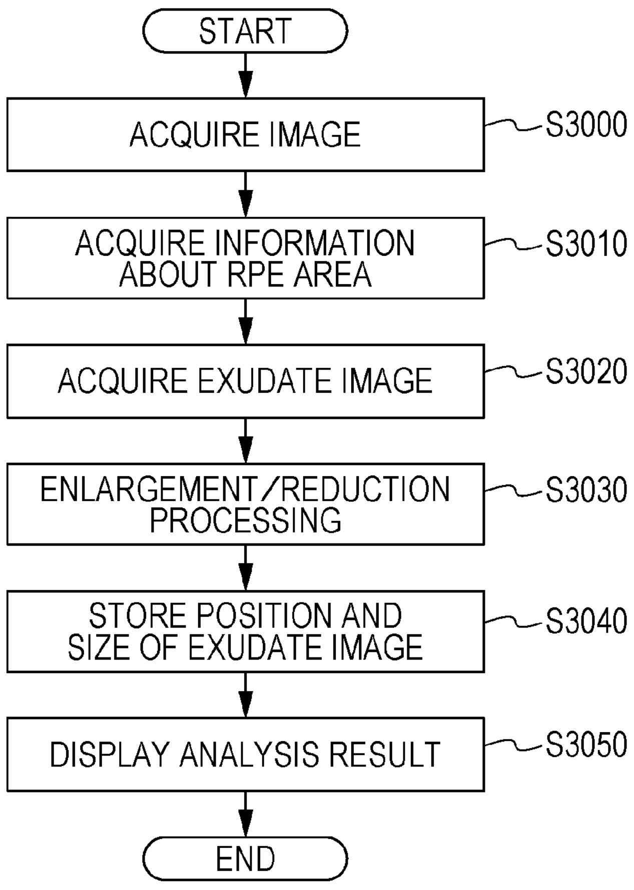
FIG. 9 is a flow chart illustrating a flow of processing according to the exemplary embodiment.

FIG. 9 is a flowchart illustrating a flow of processing in a modification example in which information about a depolarized area such as exudates is extracted.

In step S3000, the image acquisition unit 2000 acquires a plurality of three dimensional tomographic images, which are imaged at different times, each indicating the polarization state. In steps S3010 and S3020, an area extraction unit extracts information about a stored RPE layer area, removes the information about the RPE layer area from each of the three dimensional tomographic images to acquire a pixel value range in the predetermined range as information about the depolarized area such as exudates.

The analysis unit 2030 performs a processing for expanding and reducing the depolarized area such as exudates acquired from each image. In steps S3010 and S3020, the depolarized area such as exudates is extracted as an area with a certain degree of size by this processing. The analysis unit 2030 acquires the coordinates and the size of center of gravity in this area and stores them in the storage unit. A circumscribed area of the depolarized area such as exudates is acquired and a size of the depolarized area such as exudates is acquired as size. In step S3040, the coordinates of center of gravity in the depolarized area and a size of the depolarized area such as exudates are associated with images such as exudates, and information about position is associated with the imaging time and stored in the storage unit. In step S3050, the generated images and the analysis results are output.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-005393, filed Jan. 16, 2013, and No. 2014-001524, filed Jan. 8, 2014, which are hereby incorporated by reference herein in their entirety.

What is claimed is:

1. An ophthalmic apparatus, comprising:

a fundus image acquisition unit configured to acquire a plurality of fundus images acquired by imaging fundus of a subject's eye at different times and at least one fundus image that is fewer than the plurality of fundus images and acquired by imaging fundus of the subject's eye at a different time from those for the plurality of fundus images;

a generating unit configured to generate a new fundus image by averaging the plurality of fundus images;

an extraction unit configured to extract a feature region from the generated new fundus image;

a scanning unit configured to scan a measuring light in the fundus; and a control unit configured to control the scanning unit so as to correct, based on the extracted feature region and the at least one fundus image, positions of tomographic images in the fundus irradiated with the measuring light.

2. The ophthalmic apparatus according to claim 1, wherein the fundus image acquisition unit acquires the plurality of fundus images and the at least one fundus image at a frame rate equal to or higher than 60 Hz.

3. The ophthalmic apparatus according to claim 1, further comprising a tomographic image acquisition unit configured to acquire polarization-sensitive tomographic images as the tomographic images based on a plurality of lights having polarization components different from each other obtained by splitting a combined light obtained by combining a light returning from the fundus irradiated with a measuring beam via the scanning unit and a reference beam corresponding to the measuring beam.

4. The ophthalmic apparatus according to claim 3, wherein the tomographic image acquiring unit acquires the polarization-sensitive tomographic images by using the measuring light controlled so as to be scanned in same positions of the fundus.

5. The ophthalmic apparatus according to claim 1, wherein the fundus image acquisition unit is configured to acquire fundus luminance images of the subject's eye as the fundus images based on a plurality of lights having polarization components different from each other obtained by splitting a light returning from the fundus irradiated with a light.

6. The ophthalmic apparatus according to claim 1, wherein a number of frames of the plurality of fundus images is 20 or more.

7. An ophthalmic method, comprising:

acquiring a plurality of fundus images acquired by imaging fundus of a subject's eye at different times and at least one fundus image that is fewer than the plurality of fundus images and acquired by imaging fundus of the subject's eye at a different time from those for the plurality of fundus images;

generating a new fundus image by averaging the plurality of fundus images;

extracting a feature region from the generated new fundus image;

scanning, by a scanning unit, a measuring light in the fundus; and controlling the scanning unit so as to correct, based on the extracted feature region and the at least one fundus image, positions of tomographic images in the fundus irradiated with the measuring light.

8. The ophthalmic method according to claim 7, wherein the acquiring acquires the plurality of fundus images and the at least one fundus image at a frame rate equal to or higher than 60 Hz.

9. A non-transitory computer-readable storage medium configured to store a program causing a computer to execute the steps of the ophthalmic method according to claim 7.

10. An ophthalmic apparatus comprising:

a scanning unit configured to scan a measuring light in a fundus of a subject's eye;

a tomographic image acquisition unit configured to acquire, based on a plurality of lights having polarization components different from each other obtained by splitting a combined light obtained by combining a light returning from the fundus irradiated with a measuring beam and a reference beam corresponding to the measuring beam, polarization-sensitive tomographic images of the fundus, wherein the of polarization-sensitive tomographic images are imaged at different times;

a fundus image acquisition unit configured to acquire a plurality of fundus images of the subject's eye at a frame rate equal to or higher than 60 Hz; and a control unit configured to control the scanning unit so as to correct, based on the plurality of fundus images, positions of the polarization-sensitive tomographic images in the fundus.

11. The ophthalmic apparatus according to claim 10, wherein the tomographic image acquiring unit acquires the polarization-sensitive tomographic images by using the measuring light controlled so as to be scanned in same positions of the fundus.

12. The ophthalmic apparatus according to claim 10, wherein the fundus image acquisition unit is configured to acquire fundus luminance images of the subject's eye as the fundus images based on a plurality of lights having polarization components different from each other obtained by splitting a light returning from the fundus irradiated with a light.

13. The ophthalmic apparatus according to claim 10, wherein a number of frames of the plurality of fundus images is 20 or more.

14. An ophthalmic method comprising:

scanning, by a scanning unit, a measuring light in a fundus of a subject's eye;

acquiring, based on a plurality of lights having polarization components different from each other obtained by splitting a combined light obtained by combining a light returning from the fundus irradiated with a measuring beam and a reference beam corresponding to the measuring beam, polarization-sensitive tomographic images of the fundus, wherein the polarization-sensitive tomographic images are imaged at different times;

acquiring a plurality of fundus images of the subject's eye at a frame rate equal to or higher than 60 Hz; and controlling the scanning unit so as to correct, based on the plurality of fundus images, positions of the polarization-sensitive tomographic images in the fundus.

15. A non-transitory computer-readable storage medium configured to store a program causing a computer to execute the steps of the ophthalmic method according to claim 14.

* * * * *